Figure 1:
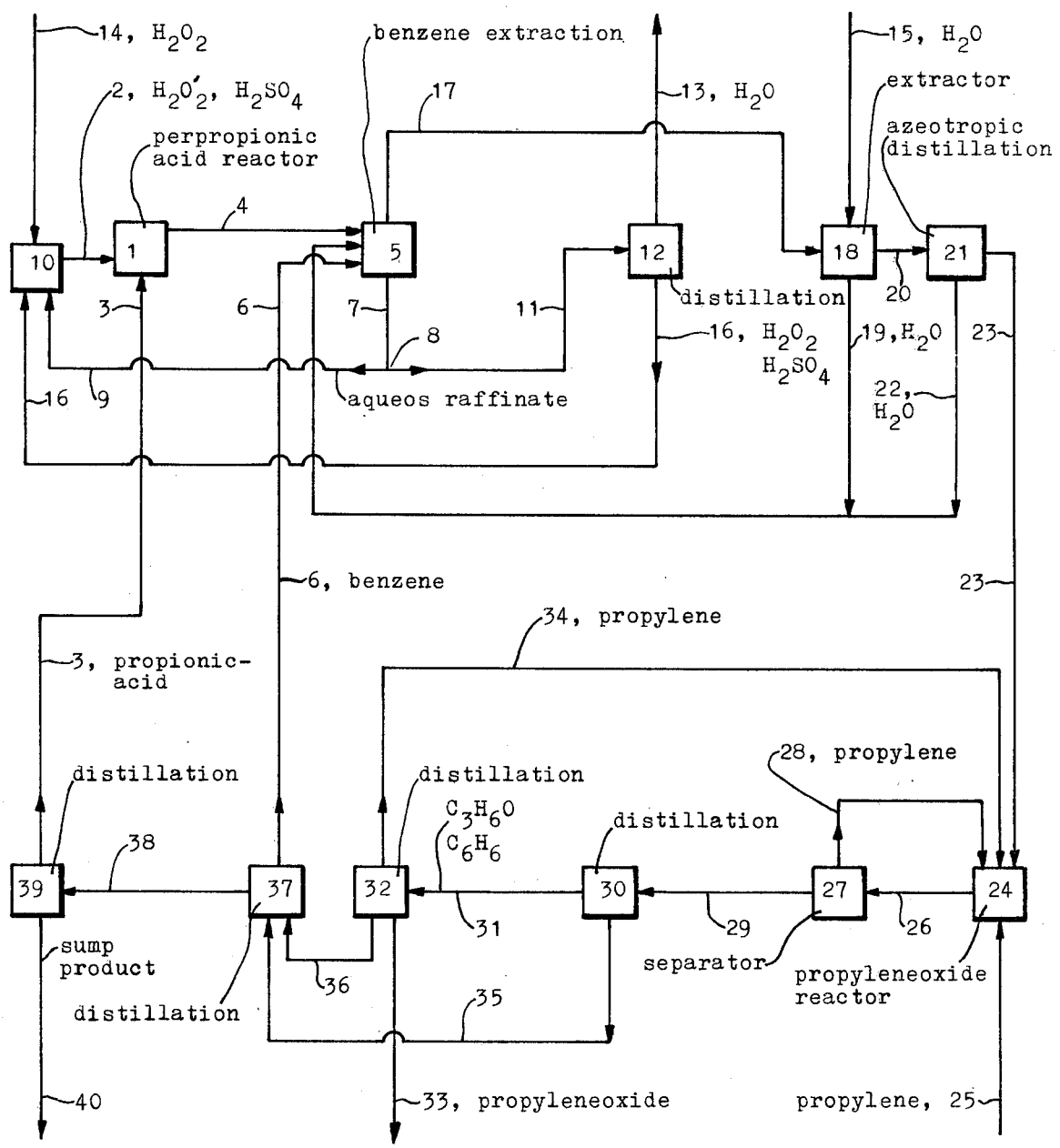

United States Patent [19]

Prescher et al.

[11] 4,137,242

[45] Jan. 30, 1979

[54] PROCESS FOR THE PREPARATION OF PROPYLENE OXIDE

[75] Inventors: Günter Prescher; Gerd Schreyer, both of Hanau; Otto Weiberg, Neu-Isenburg; Rolf Wirthwein, Hanau; Helmut Waldmann, Leverkusen; Hermann Seifert, Cologne; Wulf Schwerdtel, Leverkusen; Wolfgang Swodenk, Odenthal, all of Fed. Rep. of Germany

[73] Assignees: Bayer Aktiengesellschaft, Leverkusen; Deutsche Gold- und Silber-Scheideanstalt Vormals Roessler, Frankfurt am Main, both of Fed. Rep. of Germany

[21] Appl. No.: 678,823

[22] Filed: Apr. 28, 1976

[30] Foreign Application Priority Data

Apr. 30, 1975 [DE] Fed. Rep. of Germany ....... 2519297

[51] Int. Cl.$^2$ ............................................. C07D 301/14
[52] U.S. Cl. ............................ 260/348.25; 260/502 R
[58] Field of Search ................... 260/348.5 L, 502 R, 260/348.25

[56] References Cited

FOREIGN PATENT DOCUMENTS

| 1917031 | 10/1969 | Fed. Rep. of Germany .... 260/348.5 L |
| 2262970 | 7/1974 | Fed. Rep. of Germany ...... 260/502 R |
| 1188791 | 4/1970 | United Kingdom .............. 260/348.5 L |

Primary Examiner—Norma S. Milestone
Attorney, Agent, or Firm—Sprung, Felfe, Horn, Lynch & Kramer

[57] ABSTRACT

Process for continuous production of propylene oxide (FIG. 1) from propylene and aqueous hydrogen peroxide. The aqueous hydrogen peroxide is first reacted with propionic acid in the presence of acid catalyst to form perpropionic acid (1). The perpropionic acid is taken up by extraction in benzene (5, 18) and following drying of the benzene solution (21), the perpropionic acid in the solution is reacted with propylene (24) for oxidation of the propylene to propylene oxide and conversion of the perpropionic acid back to propionic acid. The reaction mixture is worked up to separate propylene oxide, propionic acid and benzene (30, 32, 37, 39), and the latter two are recycled. In the benzene extraction (5, 18), an aqueous raffinate (7) is formed containing hydrogen peroxide and acid catalyst. The aqueous raffinate can be divided into a stream which is recycled to the propionic acid reactor (1), and a second stream which can be distilled to remove water with the concentrate being recycled to the propionic acid reactor. (1)

32 Claims, 2 Drawing Figures

PROCESS FOR THE PREPARATION OF PROPYLENE OXIDE

The following applications are related to the process hereof for production of propylene oxide as being directed to aspects of the process, some of which are disclosed herein.

| German Serial No. | U.S. Serial No. |
|---|---|
| P 25 19 288.5 | 678,819 |
| P 25 19 300.4 | 678,820 |
| P 25 19 299.8 | 678,821 |
| P 25 19 298.7-42 | 678,822 |
| P 25 19 295.4 | 678,824 |
| P 25 19 293.2-42 | 678,825 |
| P 25 19 292.1-42 | 678,826 |
| P 25 19 291.0-42 | 678,827 |
| P 25 19 289.6 | 678,828 |
| P 25 19 297.4 | 678,829 |

All of said related applications were filed on Apr. 28, 1976.

BACKGROUND

The present invention relates to a continuous process for the industrial preparation of propylene oxide from hydrogen peroxide and propylene.

Hitherto propylene oxide has been prepared on a large industrial scale by two processes exclusively, that is either according to the older process via propylene chlorohydrin or more recently with the aid of hydrocarbon peroxides.

The older chlorohydrin process has the disadvantage that undesirable chlorinated by-products and waste salts which pollute the environment are formed (DAS (German Published Specification) 1,543,174, column 2, lines 15 et seq.).

The more recent process, used industrially, for the preparation of propylene oxide via hydrocarbon peroxides, such as is described, for example, in USA Patent Specification 3,350,422, eliminates these considerable disadvantages of the chlorohydrin process. The reaction of propylene with a hydrocarbon peroxide ROOH can be illustrated by the equation (1)

(1.)
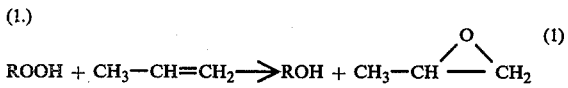

It can be seen from equation (1) that in this reaction 1 mol of the alcohol ROH corresponding to the peroxide is always formed per 1 mol of propylene oxide formed. The hydrocarbon peroxide thus effects a transfer of oxygen so that, after the release of the peroxide oxygen, the corresponding alcohol is obtained as a co-product and frequently has to be removed as an undesired by-product. Accordingly, the possibilities for industrial use of such a process are limited, since the alcohol by-product cannot be utilised in every case.

In contrast, with the principle on which the process according to the invention for the preparation of propylene oxide from propylene and hydrogen peroxide is based, the desired end product is obtained, as is shown in equation (2), free from such by-products, which either have to be eliminated at considerable expense because of their environmental pollution properties or for which a suitable further use has to be found when they are obtained as co-products.

However, the desired objective is not achieved by direct reaction of propylene with aqueous hydrogen peroxide (USA Patent Specification 3,350,422, column 2, lines 42 – 44).

On the other hand, it is known to epoxidise propylene with the aid of a percarboxylic acid to give propylene oxide (Prileschayev, Ber. dtsch. chem. Ges. 42, 4811 (1909) and D. Swern "Organic Peroxides," Wiley Interscience 1971, volume 2, page 355–533, especially page 375–378 and page 397). In addition, it is known to obtain percarboxylic acids from carboxylic acids with the aid of hydrogen peroxide (German Patent 251,802 and, for example, D. Swern, loc. cit., 1970, volume 1, page 313–369 and page 428-439). These two partial steps are illustrated in the equations (3) and (4), in which R-COOH and R-COOOH represent a carboxylic acid and a percarboxylic acid respectively.

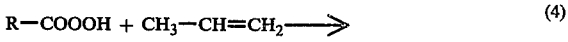

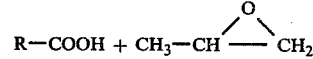

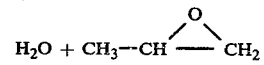

If the carboxylic acid obtained according to equation (4) is recycled into the reaction according to equation (3) to obtain percarboxylic acid, the overall equation (2) results for the reaction of hydrogen peroxide with propylene to give propylene oxide. A process of this type for the preparation of propylene oxide starting from hydrogen peroxide and propylene and using percarboxylic acids as the epoxidising agent has not hitherto been mastered in an industrially satisfactory manner and consequently has not yet been used on an industrial scale. In this connection it is stated, for example, in USA Patent Spec. No. 3,350,422 (column 1, line 65 to column 2, line 11):

"In light of the complexity and cost of the chlorohydrin route, workers have turned to other possible routes for the epoxidation of propylene and other olefins. One route which has proved successful insofar as being capable of actually producing at least limited yields of propylene oxide and other oxides is the peracid route. This route involves the formation of a peracid, such as peracetic acid, through the reaction of hydrogen peroxide with the organic acid and the epoxidation of an olefin with the peracid. The disadvantages of the peracid route also are such as to preclude significant commercialization. The peracids themselves are extremely hazardous to handle and give rise to severe operation problems. The reagents are expensive, corrosive, and nonregenerable, inasmuch as the hydrogen peroxide is lost as water. The composition of the peracid epoxidation mixture contains chemicals ($H_2O$, AcOH, and $H_2SO_4$) which are highly reactive with the product epoxides, thus leading to many by-products (glycol, glycol monoester, glycol diester) which lower the overall efficiency. This problem becomes more severe with the less reactive olefins, in particular propylene."

In fact, all the processes hitherto known for the preparation of propylene oxide from hydrogen peroxide and propylene, which proceed via the intermediate stage of a percarboxylic acid as an oxygen transfer agent, lead only to unsatisfactory yields of propylene oxide and to considerable amounts of by-products, such as propylene glycol, propylene glycol monoester and propylene glycol diester. It has also not been possible satisfactorily to overcome the extremely difficult process problems, especially with regard to the isolation of the percarboxylic acid, which are caused by the explosion hazard of the percarboxylic acids.

In the case of the process according to DOS (German Published Specification) 1,618,625, which has been disclosed more recently, for the preparation of oxiranes from olefines and hydrogen peroxide with the aid of formic acid, the measures described there are also not adequate for an industrially satisfactory production of propylene oxide from hydrogen peroxide and propylene. For this process it is necessary for the reaction mixture to be substantially free from mineral acid and substantially anhydrous or to contain only a small amount of water (DOS (German Published Specification) 1,618,625, Claim 1). Thus, it is stated, for example, on page 3, final paragraph and page 4, first line, of DOS (German Published Specification) 1,618,625: "The use of an anhydrous reaction mixture is desired, but the preparation of solutions of performic acid having less than about 0.3% of water is neither simple nor economically tenable. The use of a reaction mixture which contains only a small amount of water is preferred." An amount of less than 20 g/l is mentioned as an appropriate water content and an amount of less than 10 g/l is mentioned as being a required water content in some cases. The freedom from mineral acid, which it is attempted to achieve in the process, is important since the catalysts required for the reaction of formic acid with hydrogen peroxide also catalyse the cleavage reaction of oxirane rings, in the present case the cleavage of propylene oxide (DOS (German Published Specification) 1,618,625, page, 5 lines 10–14). Accordingly, it would be most advantageous to use in the process a solution, which as far as possible is absolutely anhydrous and as far as possible is free from mineral acid, of performic acid in a hydrophobic solvent. These requirements, particularly with regard to the freedom from water, cannot be met in the processes known hitherto, since the preparation of a non-aqueous performic acid containing only 0.3% of water or less already comes up against the difficulties mentioned in DOS (German Published Specification) 1,618,625. Accordingly, the yield of propylene oxide which can be achieved, for example, according to the process of DOS (German Published Specification) 1,618,625, is only 85%, relative to the performic acid consumed (DOS (German Published Specification) 1,618,625, Example 3). However, since the performic acid solutions still have a relatively high content of free hydrogen peroxide, this being between 3 and 10 mol % of the performic acid according to Examples 1 and 2 of DOS (German Published Specification) 1,618,625, the yield of propylene oxide, relative to hydrogen peroxide employed, is even lower, since the hydrogen peroxide contained in the performic acid solution used as the epoxidising agent can not be recovered from the mixtures, containing propylene oxide, which are obtainable from the reaction with propylene. It is not possible to determine the accurate percentage figures for the final yield of propylene oxide, relative to hydrogen peroxide employed, from the data given in the examples; however, it is less than 50%.

A further disadvantage of the process of DOS (German Published Specification) 1,618,625 is that the formic acid used as the oxygen transfer agent is a special case amongst the carboxylic acids with regard to the question of corrosion also, which is always of considerable importance in reactions with lower carboxylic acids, because formic acid is even particularly corrosive towards stainless steels. It is precisely in a process in which sensitive peroxy compounds, such as hydrogen peroxide and percarboxylic acids, are used that corrosion of any type is extremely undesirable since, due to corrosion, heavy metal compounds which cause the decomposition of hydrogen peroxide and of the percarboxylic acid are carried into the reaction.

In another more recent process for the preparation of olefine oxides from olefine and hydrogen peroxide, an aromatic carboxylic acid, preferably benzoic acid, is used as the oxygen transfer agent (DOS (German Published Specification) 2,312,281). However, in this process the problem of obtaining the percarboxylic acid by reaction of hydrogen peroxide with an aromatic carboxylic acid has not been solved satisfactorily. That is to say, the reaction mixture, containing percarboxylic acid, which is obtainable must be diluted, for further working up, with ice water and cooled ammonium sulphate solution whilst maintaining a temperature of less than 25° C and the unreacted hydrogen peroxide is then destroyed. (DOS (German Published Specification) 2,312,281, page 5, 2nd and 3rd paragraph). A further disadvantage of this process is that the rate of reaction of the aromatic percarboxylic acid with propylene is very low, since after a reaction time of 4 hours at a temperature of 28 to 30° C only 66% of the percarboxylic acid are converted. The total yield of propylene oxide, relative to hydrogen peroxide employed, is apparently very small with this process. According to Example 1 of DOS (German Published Specification) 2,312,281, the final yield for propylene oxide, relative to hydrogen peroxide employed, is about 40%.

A further process which can be used to prepare propylene oxide is the process for the oxidation propylene described in DOS (German Published Specification) 1,917,031, in which propylene is reacted with an equilibrium mixture consisting of at least one carboxylic acid, hydrogen peroxide and water, in the absence of mineral acid and heavy metal ions, the amount of water present during the reaction being so regulated that at least one compound from the group comprising propylene oxide, propylene glycol and propylene glycol esters is obtained. When carrying out the process in practice, a hydrogen peroxide solution prepared by air oxidation of a secondary alcohol, for example isopropanol, is used as the starting material for the preparation of the equilibrium mixture to be employed in the process and is treated with a urea solution in order to form a urea/hydrogen peroxide adduct, which is mixed with an extracting solvent (an alkyl ketone, alkyl ester or alkyl orthphosphate, by which means the hydrogen peroxide is dissolved in the extracting solvent, urea being deposited, and subsequently at least part of the extracting solvent in the resulting hydrogen peroxide solution is mixed with the carboxylic acid, for example acetic acid, or replaced by this (DOS (German Published Specification) 1,917,031, page 3 and also Example 1). The oxidation of propylene then carried out using the equilibrium mixture leads to the formation of propylene oxide, propylene glycol and propylene glycol esters in varying amounts (loc. cit., page 4, lines 2 and 3). The ratio of propylene oxide to propylene glycol and propylene glycol esters is regulated by the amount of water and excess carboxylic acid which remains in the equilibrium mixture containing the percarboxylic acid (loc. cit., page 5, lines 6–8). When the process is intended to give propylene oxide as the main product, it is appropriately carried out, as can be seen from DOS (German Published Specification) 1,917,031, using only a slight excess of carboxylic acid, since, as is known, the presence of larger amounts of carboxylic acid easily leads to the formation of propylene glycol and the esters thereof and not to the formation of propylene oxide (loc. cit., page 6, lines 18 to 23). This in turn means that the rate of formation of the percarboxylic acid is reduced and this has an adverse effect on the economics of the process (loc. cit., page 7, line 1 to 4). Moreover, because of the absence of mineral acid, the rate of formation of the percarboxylic acid in this process is considerably lower at all molar ratios of hydrogen peroxide to carboxylic acid than when mineral acid is present. The effect of this is, of course, very particularly disadvantageous if the excess of carboxylic acid is small. The yields of propylene oxide, relative to hydrogen peroxide employed, achieved according to this process are small, especially because the unreacted hydrogen peroxide is not recovered and the unreacted percarboxylic acid is destroyed. Because of the lack of data, the yields of propylene oxide, relative to hydrogen peroxide employed, cannot be calculated accurately from the two illustrative examples of DOS (German Published Specification) 1,917,031. However, it can clearly be seen from the data of DOS (German published Specification) 1,917,031 that the peracetic acid solution prepared according to Example 1(a) must still have contained substantial amounts of free hydrogen peroxide, so that the yield of peracetic acid, relative to the amount of hydrogen peroxide employed, can have been about 69% in the most advantageous case. Accordingly, the yield of propylene oxide, relative to hydrogen peroxide employed, of course also falls considerably, to about 64% in Example 2(b,i).

Accordingly, it can be seen from the state of the art that it has not been possible to find a technically satisfactory solution, not only in respect of the process step for the preparation of the percarboxylic acid, but in particular also in respect of the subsequent reaction of the percarboxylic acid, for example as a non-aqueous solution, with propylene to give propylene oxide. Improvements in this reaction with regard to process engineering, such as have been described in British Patent Specification 1,105,261, German Patent Specification 1,216,306 and DOS (German Published Specification) 1,923,392, also have such great disadvantages that they cannot be used for carrying out the process on an industrial scale.

The basic assumption in British Patent Specification 1,105,261 is that only yields of 75%, relative to the percarboxylic acid, are possible when this reaction is carried out by mixing the reactants, for example by mixing propylene and peracetic acid (British Patent Specification 1,105,261, page 1, lines 20 – 24).

Now it is proposed in British Patent Specification 1,105,261 to use a series of closed reaction loops, in which mixing of reaction products with the starting substances is largely prevented, for carrying out the reaction of a non-aqueous peracetic acid solution with propylene. However, the proposed process is not adequate for an economical preparation of propylene oxide from propylene and a percarboxylic acid, since the yield of propylene oxide, relative to peracetic acid employed, is only 90% and 2.5 mol% of propylene glycol monoacetate and a further 2.5 mol% of other higher boiling by-products are formed (British Patent Specification 1,105,261, page 3, lines 60–68).

Even according to the process of German Patent Specification 1,216,306, by using coiled tubes of very precise dimensions for the reaction of propylene with peracetic acid, a yield of only 86% of theory is achieved. (German Patent Specification 1,216,306, column 8, line 33).

The process according to DOS (German Published Specification) 1,923,392 is intended to improve the rate of reaction and, at the same time, to prevent side reactions and secondary reactions, because, although the rate of reaction can be increased by simply carrying out the reaction under pressure, it has not been possible to prevent the occurrence of side reactions in this way (DOS (German Published Specification) 1,923,392, page 2, lines 14 – 18). According to the process of DOS (German Published Specification) 1,923,392, an attempt is then made to eliminate these disadvantages by using a reaction system consisting of a multiplicity of reaction zones (in practice a multi-stage bubble column). However, carrying out the reaction in this way means that, due to the requisite technically highly expensive procedure, a new and considerable disadvantage has to be accepted, because the process technology for the reaction of propylene with peracetic acid in heterogeneous phase (gaseous/liquid) is far more complicated than that for a reaction in homogeneous phase.

The Invention

In contrast, it has now been found that, starting from aqueous hydrogen peroxide and propylene, propylene oxide can be prepared continuously in a manner which is advantageous from both the technical and economic point of view when (a) an aqueous solution containing 10 to 40% by weight of a water-soluble acid catalyst and 20 to 30% by weight of hydrogen peroxide is reacted with propionic acid in a molar ratio of hydrogen peroxide:propionic acid of 3.5 – 5.0 : 1 at temperatures of from 10 to 70° C, (b) the resulting reaction mixture is extracted with benzene in counter-current, (c) all or part of the aqueous raffinate from the extraction, which contains in the main hydrogen peroxide and acid catalyst, is reconcentrated by removing water by distillation, (d) the reconcentrated raffinate and the part of the raffinate which has optionally not been reconcentrated are recycled into the reaction stage (a), the concentrations of hydrogen peroxide and water-soluble acid catalyst being made up to those required for the reaction with propionic acid by adding the hydrogen peroxide required to restore the hydrogen peroxide concentration to that required for the reaction with propionic acid to the part of the raffinate which is to be reconcentrated, before or after removal of water by distillation according to (c), or to the part of the raffinate which is optionally not reconcentrated, (e) the benzene extract, which contains in the main perpropionic acid and propionic acid, is treated with water or an aqueous solution, (f) the water-containing benzene extract, which is now virtually free from hydrogen peroxide, is subjected to an azeotropic distillation so that the residual water content in the sump of the azeotrope column is less than 0.5% by weight, (g) the solution, containing perpropionic acid and propionic acid, which is now obtained as the sump product from the azeotropic distillation, is reacted with excess propylene at temperatures of from 40 to 100° C and at a pressure of from 2 to 30 bars, and (h) the reaction mixture, containing propylene oxide, is worked up in a manner which is in itself known, pure propylene oxide being isolated and the excess propylene which may be present, the propionic acid and the benzene being recovered and the whole or part of these recovered products being recycled into the process.

Step (a) —production of perpropionic acid

In the reaction according to (a) of hydrogen peroxide with propionic acid in the presence of an acid catalyst, an equilibrium is set up between propionic acid and perpropionic acid and can be shown according to the following equation:

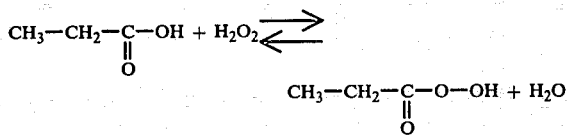

Depending on the concentration of acid catalyst, for example sulphuric acid, and hydrogen peroxide and depending on the molar ratio of hydrogen peroxide to propionic acid, about 30 to 70% of the propionic acid is converted to perpropionic acid.

In general, together with the aqueous solution containing 10 to 40% by weight of water-soluble acid catalyst, for example sulphuric acid or methanesulphonic acid, and 20 to 30% by weight of hydrogen peroxide, the propionic acid is used in the pure, undiluted form. However, it is also possible to use a propionic acid which contains water, hydrogen peroxide or an acid catalyst, it being necessary in this case to change the concentration of the aqueous solution accordingly in order to maintain the ratio of hydrogen peroxide, acid catalyst, propionic acid and water required for the reaction. Thus, for example, a mixture of propionic acid and hydrogen peroxide, for example a propionic acid containing 20% by weight of hydrogen peroxide, can be employed in place of pure propionic acid. Of course, the hydrogen peroxide content in the aqueous feed solution containing acid catalyst and hydrogen peroxide must then be adjusted according to the hydrogen peroxide content in the propionic acid, so that a total feed of hydrogen peroxide which corresponds to a hydrogen peroxide content of 20 to 30% by weight in the aqueous solution results from the hydrogen peroxide contained in the propionic acid and from that in the aqueous solution. For example, in a case where the propionic acid to be converted to perpropionic acid already contains hydrogen peroxide, the hydrogen peroxide content in the aqueous solution itself can be less than 20% by weight, for example 12 to 19% by weight. Within the indicated concentration ratios of catalyst and hydrogen peroxide, it is possible to use all conceivable mixing ratios.

Preferably, an aqueous solution containing 20 to 35, preferentially 22 to 30% by weight of acid catalyst and 22 to 28% by weight of hydrogen peroxide is used in the reaction. Particularly preferentially, it is also possible to use an aqueous solution containing 23 to 28% by weight of acid catalyst and 22 to 28% by weight of hydrogen peroxide.

In general, the reaction vessel is charged uniformly with the propionic acid and the aqueous solution of the acid catalyst and hydrogen peroxide. However, it is also possible initially to introduce all or part of the aqueous solution containing the acid catalyst and hydrogen peroxide and to add the propionic acid.

The ratio of hydrogen peroxide to propionic acid in principle is subject to no upper limit, but is preferably to be so selected that the molar ratio of hydrogen peroxide to propionic acid is 3.7 to 4.5 : 1. It is particularly advantageous to use a molar ratio of 3.9 to 4.2 : 1.

Sulphuric acid is advantageously used as the water-soluble acid catalyst. Other water-soluble acids can also be used, for example, sulphonic acids, such as methanesulphonic acid, ethanesulphonic acid, propanesulphonic acid, butanesulphonic acid, isobutanesulphonic acid, benzenesulphonic acid, toluenesulphonic acid, trifluoromethanesulphonic acid, 1-fluoroethanesulphonic acid, perfluoroethanesulphonic acid, perfluoropropanesulphonic acid or perfluorobutanesulphonic acid; phosphoric acid, phosphonic acids, such as methanephosphonic acid or ethanephosphonic acid, phosphinic acids or acid salts such as sodium bisulphate or potassium bisulphate. Mixtures of water-soluble acids can also be used. Commercially available hydrogen peroxide, for example 30 to 90% strength by weight $H_2O_2$, is used to prepare the aqueous solution. Of course, hydrogen peroxide which is obtained as a by-product from other chemical processes or as a return stream is also suitable. Acids of sulfur and phosphorus are preferred.

The reaction temperature is generally between 10 and 70° C. Appropriately, the reaction is carried out at 20 – 60° C. Temperatures below 45° C are particularly advantageous for the reaction. It is very particularly appropriate to maintain reaction temperatures of from 30 to 40° C.

In general, the reaction is carried on until the equilibrium between perpropionic acid and propionic acid is set up. However, it is also possible to discontinue the reaction before the equilibrium is reached and to feed the reaction mixture thus obtained to the next process stage, that is to say the extraction with benzene.

The pressure is not important for the reaction of propionic acid with hydrogen peroxide, so that the reaction can be carried out at normal pressure, elevated pressures or at reduced pressure. In general it is appropriate to carry out the reaction at pressures below 1.1 bars.

The reaction can be carried out in very diverse reaction vessels. It is appropriate to make provision for a steady state concentration profile and in particular to avoid so-called pockets in which parts of the reaction mixture remain for a disproportionately long time. Suitable vessels are, for example, the customary reaction tubes of varying diameter and varying length, which can also be arranged as a closed cycle for example as loop reactors, as well as stirred kettles.

Step (b) — benzene extraction

The reaction mixture from reaction stage (a) is now fed to the counter-current extraction with benzene according to (b). This counter-current extraction can be carried out in one or more extractions units. In addition to benzene, other solvents which are immiscible with water and which are inert towards the reaction mixture from reaction (a), for example hydrocarbons, such as toluene, xylene, ethylbenzene or cyclohexane; chlorinated hydrocarbons, such as methylene chloride, chloroform, 1,2-dichloroethane, 1,2-dichloropropane or 1,2-dichloro-1,2-difluoroethane; esters, such as ethyl acetate, ethyl propionate, phosphoric acid tributyl ester, phosphoric acid triisooctyl ester or methanephosphonic acid octyl ester, or ethers, such as, for example, di-(4-chlorobutyl) ether, are also suitable. For example, circulating benzene which contains less than 0.5%, preferably less than 0.1%, of propionic acid is used. The ratio of benzene to the reaction mixture to be extracted is generally 4 to 0.3 : 1. However, larger amounts of benzene can also be used. If the extraction is carried out in several extraction units, the amount of benzene can vary from unit to unit.

The perpropionic acid content in the extract can be varied within wide limits by the amount of the extraction agent and by the number of extraction stages. In general, the procedure is such that an approximately 3 to 20% strength by weight solution of perpropionic acid in benzene is obtained. Preferably, a benzene extract containing about 7 to 15% by weight of perpropionic acid is produced. Accordingly, the number of extraction stages should be as large as possible. However, in general an extraction unit with 5 to 10 theoretical extraction stages is adequate in order to prepare the solutions with the desired concentration of perpropionic acid. Preferably, however, the extraction (b) of the reaction mixture, containing perpropionic acid, obtained according to (a) is carried out in two stages as follows: the whole of the reaction mixture obtained according to (a) is extracted in a first extraction unit, which contains 2 to 6 theoretical extraction stages, in counter-current with benzene or with a benzene solution which already contains small amounts or perpropionic acid and propionic acid. The raffinate which leaves the first extraction unit and which essentially contains the hydrogen peroxide which has not been reacted according to (a), the water-soluble acid catalyst and water, is then divided in a ratio of 0.1 : 1 to 20 : 1, preferably of 1 : 1 to 10 : 1 and preferentially of 2 : 1 to 5 : 1; the smaller partial stream, thus obtained, of the raffinate from the first extraction unit is fed, for as thorough an extraction as possible, into a second extraction unit, which also comprises 2 to 6 theoretical extraction stages, where this part of the raffinate is extracted in counter current with benzene, which, as already mentioned above, preferably contains less than 0.1% by weight of propionic acid. Advantageously, the benzene extract obtained from the second extraction unit is returned, as extraction agent, to the first extraction unit, whilst the larger partial stream of the raffinate from the first extraction unit is recycled into the reaction with propionic acid according to (a) and the raffinate from the second extraction unit, which essentially is an aqueous solution containing acid catalyst and hydrogen peroxide, is subjected to reconcentration according to (c). The ratio of benzene to the smaller raffinate stream from the first extraction stage, which is to be extracted in the second extraction stage, can vary within wide limits; this ratio is preferably 0.5 : 1 to 8 : 1, preferentially 1 : 1 to 4 : 1. Of course, it is desirable to obtain the raffinate from both extraction stages as free as possible from propionic acid and perpropionic acid. However, it is generally adequate if not more than 0.2% of propionic acid and perpropionic acid remains in the raffinate from the second extraction stage.

The temperature during the extraction can be varied within wide limits. In general, the extraction is carried out at temperatures of from 10 to 70° C. Appropriately, the temperature selected is the same as that used for the reaction to obtain perpropionic acid according to (a), so that the other temperatures mentioned for reaction step (a) are also possible for the extraction (b). With regard to the pressure, the extraction can be carried out at normal pressure, reduced pressure or at elevated pressures.

Extraction units which can be used are the known extraction systems with which multi-stage counter-current extraction is possible. For example, mixer/settlers, sieve tray extractors, pulsed sieve tray columns or spray columns are suitable. However, single-stage of multi-stage centrifugal extractors can also be used.

In addition to perpropionic acid and propionic acid, the organic extract still contains small amounts of free hydrogen peroxide, water and traces of the acid used as the catalyst, for example sulphuric acid. The raffinate essentially contains the unreacted hydrogen peroxide and the acid catalyst.

Steps (c) and (d) — recovery of $H_2O_2$ from aqueous phase.

The raffinate, containing in the main water, hydrogen peroxide and, for example, sulphuric acid as the acid catalyst, from the extraction is now worked up in process step (c) for further reaction of propionic acid and hydrogen peroxide by reconcentrating all or part of it by removing water in a distillation. The amount of water to be distilled off from the raffinate streams fed to this reconcentration essentially corresponds to both the amount of water which has been formed by the reaction of hydrogen peroxide with propionic acid according to (a) and the amount of water which is introduced into the process with the fresh hydrogen peroxide which is required to replenish the amounts consumed. Water, which can contain small amounts of hydrogen peroxide, perpropionic acid and propionic acid, is obtained as the top product from the distillation. In general, the distillation is carried out under reduced pressure, for example at pressures of from 10 to 250 mm Hg, preferably 40 to 150 mm Hg, and at temperatures in the sump of from 40 to 120° C, preferably from 60 to 85° C. in general, the whole of the raffinate stream which leaves the extraction is also suitable for reconcentration if the extraction is carried out in a single extraction unit. However, it is also possible, when the extraction of the reaction mixture obtained according to (a) takes place in, for example, two extraction units, to feed both the raffinate from the first extraction stage and the raffinate from the second extraction stage to the reconcentration. If, in the case of an extraction which takes place in two extraction units, the raffinate from the first unit is divided into a larger and a smaller partial stream, each of these amounts is, in principle, suitable for reconcentration. Advantageously, when the extraction consists of 2 extraction units and the raffinate leaving the first unit is divided into a small and a larger partial stream and the smaller amount is passed into the second unit, the raffinate from the second extraction unit is subjected to distillation for reconcentration.

The fresh hydrogen peroxide for replenishing the amounts consumed can be added in any desired concentration. It is appropriate to use a commercially available hydrogen peroxide, for example 30 to 90% strength by weight aqueous hydrogen peroxide, to which the customary stabilisers can be added. For example, stabilisers such as are mentioned in Gmelins "Handbuch der anorganischen Chemie" ("Handbook of Inorganic Chemistry"), 8th edition, oxygen volume, section 7, 1966, on page 2274 and page 2275, are suitable.

The fresh hydrogen peroxide can be mixed, prior to entry into the distillation unit, with the raffinate, to be reconcentrated, from the extraction according to process stage (b); the two mass flows can also be fed separately into the distillation unit. It is also possible to add the fresh hydrogen peroxide to the raffinate after this has been reconcentrated. However, the fresh hydrogen peroxide can also be fed directly into the reaction according to (a) or can be admixed to that part of the raffinate from the extraction which does not pass to reconcentration. Appropriately, a column provided with a condenser and an evaporator unit is used as the distillation unit.

The known trayed columns or packed columns can be used for the distillation. The number of distillation stages is so selected that the top product contains as little hydrogen peroxide as possible. It is desirable to obtain less than 0.1% by weight of hydrogen peroxide in the condensate. In principle, the known evaporators are suitable as the evaporator unit. For example, those evaporator units in which the residence time of the product is less than 20 minutes, preferably less than 10 minutes, are suitable. Falling flow evaporators or thin layer evaporators are particularly suitable. Suitable materials for the distillation unit are high-alloy, high grade stainless steels which, in addition to iron, also contain in the main chromium and nickel, such as, for example, a material with the DIN designation 1.4571, which, in addition to iron contains 17.5% by weight of chromium, 11.5% by weight of nickel, 2.25% by weight of molybdenum and up to 2% by weight of manganese, up to 1% by weight of silicon, up to 0.1% by weight of carbon and small amounts of titanium, or a material which, in addition to iron, contains 25% by weight of chromium, 25% by weight of nickel, 2.25% by weight of molybdenum and up to 2% by weight of manganese, up to 1% by weight of silicon, up to 0.06% by weight of carbon and also small amounts of titanium and which is designated according to DIN by the number 1.4577. Zirconium, materials containing zirconium and zirconium alloys are particularly suitable as the material for the distillation unit, especially for the evaporator.

The sump product from this distillation unit is fed back into the reaction stage (a), the concentrations of hydrogen peroxide and the catalyst being restored, as appropriate, to those required for the reaction with propionic acid. By reason of this measure of recycling the raffinate from the extraction into the reaction stage (a), all or part of the raffinate previously having passed through the reconcentration (c), a circulation of hydrogen peroxide and catalyst, which essentially comprises the process stages (a), (b) (c) and (d), is obtained. It can be appropriate to remove part, for example 0.1 to 6% by weight, of the circulating flow from the process as a side stream from time to time or continuously. Advantageously, this side stream is withdrawn at a point in the process where the concentration, in the circulating stream, of hydrogen peroxide and acid catalyst and of any perpropionic acid and propionic acid which may be present is as low as possible. The raffinate from the extraction before fresh hydrogen peroxide has been added and before reconcentration according to (c) has been effected is very particularly suitable for this withdrawal as a side stream. This side stream, which is part of the circulating flow and is an aqueous solution which essentially contains hydrogen peroxide and acid catalyst can either be discarded or can be fed into a regeneration stage for working up. For example, this part of the circulating stream can be regenerated by distilling off the hydrogen peroxide contained therein in vacuo with steam, an aqueous solution of the acid catalyst being obtained as the distillation residue. The aqueous solution, containing hydrogen peroxide, obtained as the distillate can be fed back into the process, if appropriate after reconcentration. After purification, for example by distillation, the aqueous solution of the acid catalyst can also be fed back into the process. By means of this exchange in the circulation, a corresponding part of the catalyst, for example the sulphuric acid, is withdrawn from the process and thus has to be replenished in the process. It is appropriate to replenish the sulphuric acid by adding the required amount of $H_2SO_4$ in the form of a mixture of sulphuric acid and aqueous hydrogen peroxide, it being appropriate to use the amounts of hydrogen peroxide and sulphuric acid which are obtained from the regeneration of the side stream of the circulation and can be made up, as required, by means of additional fresh feed amounts of hydrogen peroxide and sulphuric acid. However, the entire amount of aqueous solution, containing hydrogen peroxide and sulphuric acid, required to replenish the circulation, can also be prepared from fresh hydrogen peroxide and fresh sulphuric acid.

Step (e) — water treatment of benzene extract

The benzene extract which essentially contains perpropionic acid and propionic acid and which is obtained according to process stage (b) is treated in process step (e) with water or an aqueous solution. In general the procedure is such that the benzene extract containing perpropionic acid is washed with water in one of the devices customary for this purpose. It is appropriate to carry out this washing as an extraction, for example as a multi-stage counter-current extraction, with water, for example in a three-stage extraction unit. Of course, a co-current extraction or cross-current extraction can also be used in place of counter-current extraction. When working with several extraction stages, the extraction can also be carried out partially as co-current extraction and partially as counter-current extraction.

Appropriately, 0.1 to 5% by volume of water or aqueous solution, relative to the benzene extract, are used. Preferably, 0.5 to 3% by volume of water are used. In place of pure water, it is also possible to use an aqueous solution which is substantially free from hydrogen peroxide and from mineral acid. It is appropriate to use an aqueous phase which is obtained in the process. For example, the aqueous phase from the azeotropic distillation according to (f) is suitable. The aqueous phase from the water treatment can be fed back into the extraction with benzene according to (b) in order to obtain for the process the amounts of perpropionic acid and hydrogen peroxide contained therein.

The known extraction systems, for example mixer/settlers, sieve tray extractors, pulsed sieve tray columns or extraction centrifuges, are suitable as equipment for the water treatment according to process stage (e).

Step (f) — azeotropic distillation

In this way, a benzene solution which contains perpropionic acid and which is substantially free from hydrogen peroxide and from sulphuric acid is obtained and is then subjected to azeotropic distillation according to process stage (f). In this stage the water contained in the benzene solution of perpropionic acid is removed. In general, the amount of distillate is so selected that the residual water content in the sump of the azeotrope column is less than 0.5% by weight, preferably less than 0.1% by weight. However, it is also possible to reduce the water content to a negligibly small value. The benzene which separates off as the organic phase after condensation of the top vapours from the azeotrope column is returned as reflux to the column. The aqueous phase which is obtained after condensation of the top vapours and which generally contains small amounts of perpropionic acid, propionic acid and also hydrogen peroxide, is fed back into the process at a suitable point, for example at the extraction according to (e) or (b); however, it can also be withdrawn from the process. The azeotropic distillation (f) can be carried out at normal or reduced pressure, for example at 100 to 400 mm Hg. The sump temperature is, for example, 30 to 80° C. In general, a sump temperature of below 70° C is adequate.

The customary columns, for example the known trayed or packed columns, are suitable for the azeotropic distillation. The customary equipment can be used as the evaporator. Falling flow evaporators or thin layer evaporators are preferred suitable equipment.

Step (g) — the oxidation of propylene oxide

The solution, which is thus obtained as the sump product from the azeotropic distillation, of a perpropionic acid which is substantially anhydrous and free from hydrogen peroxide, in benzene is reacted in process stage (g) with an excess of propylene, for example in a molar ratio of propylene : perpropionic acid of 1.01 to 8 : 1, at temperatures of from 40 to 100° C and at pressures of from 2 to 30 bars. The reaction can also be carried out at a pressure of from 2.5 to 20 bars. Pressures of from 4 to 18 bars, for example, constitute a suitable pressure range. Preferably, the reaction is carried out at a pressure of from 5 to 14 bars. The reaction temperature is preferably kept at 60°-80° C. In addition to the procedure under isothermal conditions, that is to say maintaining a uniform temperature in the entire reaction mixture, a procedure is also possible with which a so-called temperature gradient, which generally increases as the reaction progresses, is set up in the reaction. However, the reaction can also be carried out in such a way that a falling temperature gradient is set up as the reaction progresses.

Appropriately, the pressure when carrying out process step (g) is so selected that the reaction mixture is in the main present in the liquid phase. At a molar ratio of propylene : perpropionic acid of, for example, 2.5 : 1 and at a reaction temperature of 65 to 75° C, the pressure is, for example, 6 to 8 bars.

The molar ratio of propylene to perpropionic acid is preferably 1.5 to 4 : 1. It is very particularly advantageous to use a molar ratio of 2.0 to 3.0 mols of propylene per mol of perpropionic acid.

The equipment customary for reactions of this type, such as stirred kettles, tube reactors, loop reactors or looped reactors, can be used for carrying out the reaction. In general, equipment is used which acts as a cascade of at least two ideally mixed kettles. It is particularly advantageous to use a reaction system which acts as a cascade of 4 to 50, preferably 10 to 30, ideally mixed kettles. When actually carrying out the reaction, for example, a train of several stirred kettles, for example a cascade of from 3 to 6 kettle reactors, is used.

In general, technical grade propylene is used for the reaction according to the process step (g). It can contain the impurities customary in industrial use, in particular propane. Of course, specially purified propylene, for example propylene containing less than 0.5% of propane, can also be used.

The propylene can be introduced into the reaction unit in different ways. The propylene can be employed in the liquid or gaseous form. The propylene can also be passed together with the perpropionic acid solution into the reactor unit. The two feed materials can also be introduced into the reactor separately from one another. It is further possible to pass the propylene and the perpropionic acid solution into the reactor unit at different points. When using several reactors arranged in a cascade, it can be appropriate to introduce all of the propylene into the first reactor. However, the propylene can also be divided between the various reactors.

The considerable heat of reaction is removed by internal and external coolers. In order to remove the heat of reaction, the reaction can also be carried out under reflux (boiling reactors). Appropriately, the reaction is carried out with as complete as possible a conversion of the perpropionic acid. In general, more than 98% of the perpropionic acid is converted. It is appropriate to convert more than 99% of the perpropionic acid. The reaction can be carried out with a particularly high selectivity if it is carried out partially in a reaction tube in which there is turbulent flow, the reaction tube being connected, for example, to the train of stirred kettles. It is particularly advantageous to use a reaction tube which is provided with inserts which largely prevent back-mixing, for example perforated baffle plates. For example, the reaction is carried out first in several, for example 1 to 3, stirred reaction units arranged in series and the reaction mixture is then passed into a reaction tube in order to complete the reaction. The reaction tube can be operated under adiabatic conditions; however, it is also possible to cool, for example by means of external cooling, or to fit coolers between individual sections of the tube. The dimensions of a suitable reaction tube depend on the intended throughput. It is essential that the flow velocity in the reaction tube is so high that back-mixing of the reaction components is substantially excluded. The diameter of the reaction tube can be 0.01 to 10 meters for a length of 1 to 200 meters. It is also possible to operate several tubes in parallel. For example, a tube bundle can be employed. If a reaction tube with perforated baffle plates is used, the baffle plates are generally at a distance of from 0.1 to 5 m from one another.

When the reaction between propylene and perpropionic acid (step g) is carried out according to the invention it is possible to achieve yields of propylene oxide of more than 97%, relative to perpropionic acid employed. The amount of byproducts, for example propylene glycol, propylene glycol monoester and propylene glycol diester, is less than 1 mol%, for example 0.5 mol% of less, relative to propylene oxide formed.

Step (h) —working up

The reaction mixture is worked up in a manner which is in itself known. The aim of the working up is to obtain pure propylene oxide and optionally to isolate excess propylene, propionic acid and the organic solvent in a degree of purity such that it is possible to recycle these into the process.

The reaction mixture is generally worked up by distillation. It is appropriate to separate propylene oxide and propionic acid from one another very rapidly. For this purpose, for example, a distillation column is used in which propylene oxide, optionally together with lower boiling constituents and part of the solvent, is first taken off over the top and the remaining solvent and the propionic acid are obtained as the sump product. The top product is further worked up, for example in a further distillation, in order to isolate pure propylene oxide. The organic solvent (benzene) and propionic acid are recovered from the sump products from these two distillation columns. The distillation residue from the distillation of propionic acid is the small amount of high-boiling constituents, which has already been mentioned. In principle, the solvent benzene can be recovered quantitatively.

Embodiments

One embodiment of the process according to the invention is explained with the aid of FIG. 1.

An aqueous solution containing 22 to 28% by weight of hydrogen peroxide and 23 to 28% by weight of sulphuric acid is fed via (2) and, at the same time, propionic acid is fed via (3), in a molar ratio of hydrogen peroxide to propionic acid of 3.9 to 4.2 : 1, at a temperature of 25 to 45° C, into the first reaction stage (1). The residence time in reaction system (1) is 10 to 30 minutes. The reaction mixture which leaves reaction system (1) via (4) contains about 7 to 11% by weight of perpropionic acid, 4 to 7% by weight of propionic acid, 19 to 23% by weight of sulphuric acid, 0.5 to 2% by weight of Caro's acid and 18 to 22% by weight of hydrogen peroxide. It passes into an extraction system (5), which consists of a pulsed sieve tray column with 70 to 100 sieve trays and which is charged via (6) with benzene which has a propionic acid content of less than 0.1% by weight. The ratio of benzene to the reaction mixture to be extracted, which comes from (1), is 0.3 to 2 : 1. Thus, the content of perpropionic acid in the extract can be regulated within wide limits by means of the amount of benzene used and is 6 to 12% by weight. The raffinate from this extraction, which is withdrawn from system (5) via (7), contains the hydrogen peroxide which was not converted in reaction system (1) and the sulphuric acid as well as the Caro's acid, which, in mixtures containing sulphuric acid and hydrogen peroxide, is always formed in small amounts from these components, and small amounts of perpropionic acid and propionic acid. This raffinate from the extraction is divided at (8) in a ratio of 2 : 1 to 5 : 1 into a larger and a smaller partial stream. The larger partial stream of the raffinate is fed via line (9) to the mixing vessel (10) and the smaller raffinate stream is fed via (11) to the distillation unit (12). In the distillation unit (12), which consists of an evaporator and a column, water is taken off over the top at a pressure of 40 to 120 mm Hg and a sump temperature of 60 to 85° C and this water is withdrawn from the process via (13). The amount of water which is removed as the distillate via (13) essentially corresponds to the amount of water which is contained in the fresh hydrogen peroxide which is required to replenish the amounts of hydrogen peroxide consumed and which is fed into the process via (14) plus the amount of water which is formed in reaction stage (1) plus the amount of water which serves as washing water for the benzene extract and which is fed into the process via (15). The distillate which is taken off via (13) contains small amounts of perpropionic acid, propionic acid and hydrogen peroxide. A falling flow evaporator is used as the evaporator unit for the distillation column (12). An aqueous solution, which essentially contains hydrogen peroxide and sulphuric acid, is obtained as the sump product from the reconcentration, effected in (12), of the stream of raffinate fed in via (11). The concentrations of hydrogen peroxide and sulphuric acid in this aqueous solution, which is fed via (16) to (10), are determined by the amount of water which is to be distilled off from the mass flow (11) in (12) and by the amount of the raffinate stream (11) itself which is passed to reconcentration. Accordingly, the concentrations of hydrogen peroxide and sulphuric acid prevailing in (16) are determined exclusively by the ratio which is selected at (8) for the division of the raffinate from the extraction. The benzene extract of perpropionic acid from extraction system (5) is fed via (17) into the extraction system (18), where the extract is extracted in counter-current with the water fed in via (15). Extraction system (18) consists of a pulsed sieve tray column, which comprises 1 to 5 theoretical extraction stages. The amount of water introduced via (15) into (18) is 0.5 to 2% by volume of the benzene solution. The aqueous phase from extraction unit (18) is returned via (19) into extraction system (5). The benzene solution of perpropionic acid, treated with water in this way, passes via (20) into the distillation unit (21), where an azeotropic dehydration is carried out. The pressure inside the distillation system (21) is 100 to 300 mm Hg and the sump temperature is 50 to 75° C. The water content of the benzene solution of perpropionic acid which flows out of the sump of this column, which is heated by a falling flow evaporator, is less than 0.1% by weight. The water which, after condensation, is separated out of the top vapours from the column of the distillation unit (21) is combined, via (22), with (19) and thus returned to the extraction system (5). The benzene solution of perpropionic acid, which is substantially anhydrous and free from hydrogen peroxide and which is obtained as the sump product from the azeotropic distillation, is fed via (23) into the reaction system (24), where the reaction with propylene, which is fed into the system via (25), takes place in a molar ratio of propylene to perpropionic acid of 1.1 to 3 : 1. The pressure in (24) is 4 bars. The reaction system (24) consists of two loop reactors in series with a downstream delay tube 10 to 80 m in length. The temperature in the two loop reactors, in which the reactants are mixed by means of circulation pumps, is 50 to 80° C. 80 to 95% of the perpropionic acid is converted inside the two loop reactors. The further reaction of the perpropionic acid up to a conversion of 99.8% takes place in the downstream delay tube, which is operated without cooling. The resulting reaction mixture is transferred via (26) into a receiver (27), where it is let down. The gas phase, thus obtainable, essentially contains propylene, which is recycled via (28) into the reaction with perpropionic acid, that is to say into reaction system (24). Propylene oxide is next separated, together with residual propylene and with part of the benzene, by distillation from the liquid phase which passes via (29) into the distillation unit (30). The stream containing propylene, propylene oxide and benzene is fed via (31) to the distillation unit (32), where further separation of the components takes place and pure propylene oxide is obtained, which leaves the process via (33). Propylene is recycled via (34) into the reaction system (24). The sump products from columns (30) and (32) are fed via (35) and (36) to a further distillation unit (37), where benzene is recovered as the top product and is recycled via (6) into extraction system (5). The sump product, which essentially consists of propionic acid, from the benzene recovery column (37) is fed via (38) to the distillation unit (39), in which propionic acid is distilled off as the top product, this propionic acid being recycled via (3) into the reaction system (1). The products which boil higher than propionic acid are obtained as the sump product from the distillation (39) and are withdrawn from the process via (40).

According to the process of the invention, propylene oxide can be prepared in yields of at least 94%, relative to hydrogen peroxide employed, and of at least 97%, relative to propylene employed.

The advantages of the process according to the invention can be summarised as follows:
1. Excellent economics due to the high yields;
2. no by-products which pollute the environment, such as, for example, in the case of the chlorohydrin process;
3. no co-products such as, for example, in the case of the processes which use hydrocarbon peroxides as the oxidising agent for propylene;
4. negligible amounts of by-products, such as propylene glycol, propylene glycol monopropionate or propylene glycol dipropionate;
5. less technical efforts due to simple process measures; and
6. virtually complete elimination of the explosion hazard, due to the headling of peroxy compounds, as is required for large scale industrial processes.

Figure 2:
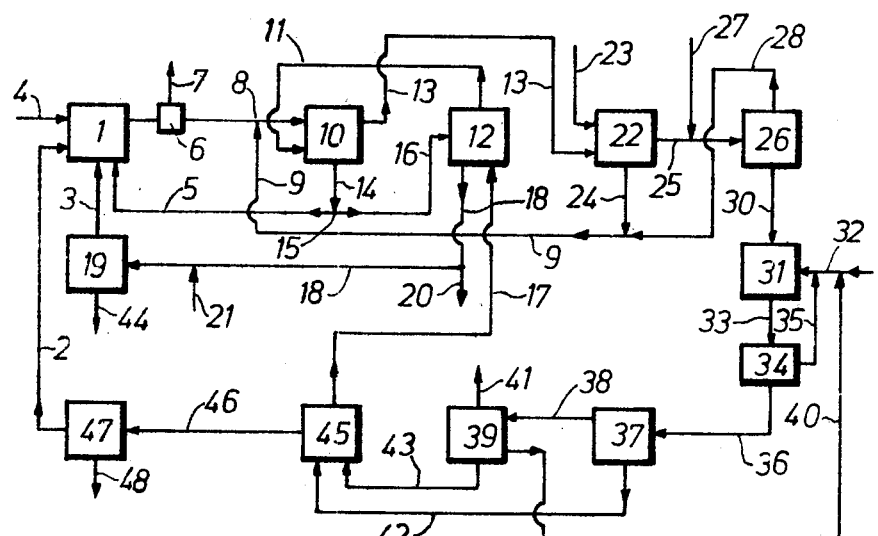

EXAMPLE 1 (see FIG. 2)

In continuous operation, 260.1 g per hour (= 3.51 mol/hour) of propionic acid are fed via line (2), 540 g/hour of an aqueous solution containing 31.7% by weight of sulphuric acid, 26.98% by weight of hydrogen peroxide and 1.28% by weight of Caro's acid, are fed via line (3), 136.4 g per hour of a 50% strength by weight aqueous solution of hydrogen peroxide (= 68.2 g/hour of $H_2O_2$ = 2.0 mol/hour) are fed via line (4) and an aqueous solution, which contains 24.65% by weight of sulphuric acid, 21.21% by weight of hydrogen peroxide, 1.0% by weight of Caro's acid, 1.52% by weight of propionic acid and 2.25% by weight of perpropionic acid, is fed, in an amount of 1,620.3 g per hour, via line (5) into the reaction system (1), which consists of a delay tube which can be heated, which is provided with packing and which has a length of 60 cm and a diameter of 5 cm. The molar ratio of hydrogen peroxide to propionic acid in the mixture of the above mentioned product streams, which passes into the reaction system (1), is 4 : 1, the hydrogen peroxide which is bound in the Caro's acid and also the amounts of $H_2O_2$ which are bound in the perpropionic acid which is contained in small amounts in stream (5) being calculated as free $H_2O_2$.

Inside reaction system (1), the mixture obtained from product streams (2), (3), (4) and (5) is warmed to 40° C for 18 minutes, the equilibrium between propionic acid and hydrogen peroxide on the one hand a perpropionic acid and water on the other hand being set up in such a way that 55% of the propionic acid fed in via (2) is converted to perpropionic acid. After passing through the delay tube (1), the product stream, which contains, on average, 8.23% by weight of perpropionic acid, 5.54% by weight of propionic acid, 22.31% by weight of sulphuric acid, 0.9% by weight of Caro's acid, 19.23% by weight of hydrogen peroxide and 43.79% by weight of water and which is obtained in an amount of 2,557.2 g per hour, is cooled to room temperature and fed into a gas separator (6), where 150 ml per hour of a gas consisting of 88% by volume of oxygen and 12% by volume of carbon dioxide are separated off and removed via (7). The degassed reaction mixture is then fed, after it has been combined at (8) with 46 g per hour of an aqueous solution, which contains 14.09% by weight of perpropionic acid, 8.96% by weight of propionic acid and 8.93% by weight of hydrogen peroxide and which is fed in via line (9), to the extraction system (10). The extraction process is carried out at a temperature of 20° C. A pulsed sieve tray column, which is provided with 40 sieve trays, which has a length of 2 m and a diameter of 2.5 cm and which is fitted at both the upper and the lower end with one separating vessel in which the phase separation takes place, is used as the extraction system (10). The mixture resulting after the combination of product stream (9) with the stream leaving the separator (6) is fed, in an amount of 2,603.3 g per hour, at the upper end of the column, below the separating vessel, and flows, as the heavy phase, through the column from top to bottom, whilst a benzene solution, which serves as the extraction agent and which contains 0.97% by weight of perpropionic acid, 0.64% by weight of propionic acid, 0.22% by weight of water and also traces of hydrogen peroxide and which has been withdrawn as the benzene extract from the subsequent extraction unit (12), is fed via line (11) to column (10) at the lower end of this column (10). A benzene solution of perpropionic acid, which in addition to 9.78% by weight of perpropionic acid, still contains 6.56% by weight of propionic acid, 0.62% by weight of water, 0.27% by weight of hydrogen peroxide and also traces of sulphuric acid, is withdrawn, in an amount of 1,838.7 g per hour, from the upper separating vessel of column (10) via line (13).

The raffinate from the extraction which takes place in (10) collects as the heavy phase in the lower separating vessel and is removed continuously from there via line (14) in an amount of 2,314.6 g per hour. This raffinate contains, on average, 24.65% by weight of sulphuric acid, 21.21% by weight of hydrogen peroxide, 1.0% by weight of Caro's acid, 49.37% by weight of water and also 2.25% by weight of perpropionic acid and 1.52% by weight of propionic acid and is divided at (15) in a ratio of 7 : 3 into a larger and a smaller stream. The larger of these two partial streams of the raffinate is recycled via line (5) to the reaction system (1), whilst the smaller stream is fed via (16) to extraction unit (12) and introduced at the upper end of (12). Like (10), unit (12) consists of a pulsed sieve tray column which is provided with separating vessels, which has a length of 2.5 m and a diameter of 20 mm and in which the 50 actual trays are fitted equal distances apart. The benzene, which is fed via line (17) in an amount of 1,522 g per hour and which serves as the extraction agent and can contain small amounts of propionic acid and water, is introduced at the lower end of column (12). Thus, the smaller partial stream (16) of the raffinate from the extraction unit (10) is extracted in counter-current with benzene in unit (12). The benzene solution (11) is obtained as the extract from this extraction, which is carried out at room temperature, and is fed to column (10), whilst an aqueous solution which contains 25.7% by weight of sulphuric acid, 22.11% by weight of hydrogen peroxide, 1.04% by weight of Caro's acid and also 0.09% by weight of perpropionic acid and 0.08% by weight of propionic acid is withdrawn, in an amount of 666 g per hour, from the lower part of the column via (18) as the raffinate from the extraction which takes place in (12). This raffinate stream (18) is further worked up to recycle to the reaction unit (1) and thus for the reaction with propionic acid, by reconcentrating it by distilling off water. This reconcentration process takes place in distillation column (19), which is operated at a pressure of 40 mm Hg and which consists of a column (length 1 m, diameter 50 mm) provided with a bubble cap trays, a condenser, a device which enables the reflux ratio to be varied, and a falling film evaporator, which can be heated by the vapours of a boiling liquid. The raffinate stream (18) is fed into the lower part of the column. At a sump temperature of 60 – 63° C, a temperature at the top of the column of 32° C and a reflux ratio (reflux/take-off) of 0.7, 124.5 g per hour of distillate, which in addition to water still contains 0.52% by weight of perpropionic acid and 0.43% by weight of propionic acid, are obtained and are withdrawn from the process via line (44). 540 g per hour of an aqueous solution, which in turn contains 31.7% by weight of sulphuric acid, 26.98% by weight of hydrogen peroxide and 1.28% by weight of Caro's acid are withdrawn from the sump of column (19) via line (3) and, after cooling to 30° C, are recycled to reaction system (1).

1.54 g per hour are withdrawn, as the raffinate from the extraction column (12) vialine (20) from stream (18) of the circulation of sulphuric acid and hydrogen peroxide, which is thus set up and which comprises the reaction system (1), the separator (6), the extraction units (10) and (12) and the distillation unit (19), and are passed to a suitable use or are regenerated. The amounts of sulphuric acid and hydrogen peroxide thus withdrawn from the circulation are replenished by feeding continuously the same amount per hour of a mixture, which has the composition of this raffinate (stream (18)) and which is prepared from aqueous solutions of sulphuric acid and hydrogen peroxide of appropriate concentrations, into the distillation column (19) via line (21), directly before the product stream (18) enters into the distillation column (19). The loss of hydrogen peroxide which results from this exchange in the circulation is 0.5%, relative to the fresh hydrogen peroxide fed into the process via (4), this of course being the case only when the amounts of hydrogen peroxide withdrawn with (20) are not regenerated and thus cannot be used to prepare the replenishing solution to be fed in via (21).

The benzene solution of perpropionic acid which is withdrawn, as the light phase, from extraction system (10) via (13) is fed into extraction system (22), where it is extracted in counter-current with water, this being effected in such a way that the organic phase coming from (10) is fed in at the lower end of the extraction system (22), which is designed as a pulsed sieve tray column (length 1.50 m, diameter 20 mm), whilst deionised water, which is fed to column (22) via line (23), enters at the upper end of the column in an amount of 20 g per hour. A mixture which contains 18.95% by weight of perpropionic acid, 12.6% by weight of propionic acid, 12.32% by weight of $H_2O_2$ and 56.13% by weight of water is obtained as the aqueous phase, in an amount of 32 g per hour, and is withdrawn from the sump of the column via line (24). 1,826.7 g per hour of a benzene solution which contains 9.51% by weight of perpropionic acid, 6.38% by weight of propionic acid, 0.06% by weight of hydrogen peroxide and 0.73% by weight of water are withdrawn from the separating vessel located at the top of column (22) and fed via line (25) to distillation unit (26), where the solution is dried azeotropically. A 50 cm long column, 50 mm in diameter, which is provided with 5 bubble cap trays and with a thin layer evaporator, a condenser and also a separator for phase separation of the distillate at the top of the column, is used as the distillation unit (26). 5 ml per hour of an approximately 3% strength by weight solution, in propionic acid, of a stabiliser of the type of the commercially available sodium salts of polyphosphoric acids which are partially esterified with long-chain alcohols are added to the benzene solution (25) before this enters into the thin layer evaporator of column (26). The stabiliser solution is fed into product stream (25) via line (27). The temperature in the sump of column (26), which is operated at a pressure of 250 mm Hg, is 62 – 65° C. 14 g per hour of an aqueous solution, which contains 2.98% by weight of perpropionic acid and 0.6% by weight of propionic acid as well as 1.19% by weight of hydrogen peroxide, and about 230 ml per hour of benzene are obtained as the distillate. The benzene is passed to the column as reflux, whilst the aqueous phase which is obtained in the separator at the top of the column is withdrawn via line (28) and combined, at (29), with the heavy phase (24) from extraction column (22) to give stream (9), after which the latter is fed, in the amount already indicated, at (8), before extraction system (10), into the mixture leaving separator (6). A 9.53% strength by weight benzene solution of perpropionic acid, which also contains 6.69% by weight of propionic acid as well as 0.05% by weight of hydrogen peroxide, is obtained, in an amount of 1,817.7 g (= 2,011 ml) per hour, as the sump product from this azeotropic distillation which takes place in (26) and is withdrawn via line (30).

The yield of perpropionic acid in the benzene extract dried in this way is 96%, relative to the hydrogen peroxide fed into the process.

The dried benzene solution of perpropionic acid, which is withdrawn from the sump of column (26) via (30), is reacted, in the reaction unit (31), which is designed as a three-stage kettle cascade, with excess propylene, which is fed via line (32). The reaction is carried out at a pressure of 4 bars. The excess of propylene, relative to the perpropionic acid which passes into the reaction, is 180 mol% (= 145.5 g of propylene per hour). The first reactor of this three-stage cascade, which, like the two downstream reaction vessels, is provided with a stirring device, and which has a capacity of 2 l, is operated at a temperature of 65° C and the second and third reactors, which also each have a volume of 2 l, are both operated at a temperature of 70° C. The average residence time for the reaction mixture formed from the perpropionic acid in benzene and the propylene is about 2.7 hours over the three reactors. The propylene is introduced in the gaseous form into the first and second reactors, 61.1% of the total amount to be fed in (3.465 mols of propylene per hour) passing into the first reactor, so that the molar ratio of propylene to perpropionic acid in that reactor is always 1.1 : 1.

Under these reaction conditions 99.8% of the perpropionic acid in the feed is converted. After the third reactor, the reaction mixture, which is obtained in an amount of 1,963.3 g/hour and which contsins, on average, 77.53% by weight of benzene, 5.61% by weight of propylene oxide, 13.4% by weight of propionic acid and also 3.32% by weight of propylene, 0.04% by weight of propylene glycol monopropionate and 0.03% by weight of propylene glycol in addition to traces of water, ethanol, carbon dioxide and oxygen, is cooled to room temperature and fed via line (33) to separator (34), where it is let down to normal pressure. This releases from the reaction mixture part of the excess propylene and also small amounts of other compounds which are no longer dissolved in the mixture under these pressure and temperature conditions. The propylene released as a gas in separator (34) is fed back into reaction system (31) via lines (35) and (32) in an amount of 45 g per hour. The mixture, containing propylene oxide, which has let down to normal pressure and leaves the separator (34) via line (36) is separated in a downstream distillation train, all of the propylene oxide, together with the propylene still dissolved in (36) and part of the benzene, being distilled out of product stream (36) in distillation column (37). The distillate, which is obtained in (37) in an amount of 202.7 g per hour and which contains 9.95% by weight of propylene, 54.36% by weight of propylene oxide and also 35.58% by weight of benzene and 0.16% by weight of water, is fed via line (38) to distillation column (39), where 110.3 g per hour of a 99.9% strength by weight propylene oxide as well as 20.2 g per hour of propylene are obtained. This propylene which is recovered in (39) is recycled via (40) into reaction system (31). The propylene oxide is withdrawn from column (39) via (41). The sump products from columns (37) and (39) are fed via lines (42) and (43) respectively to distillation column (45), where benzene is recovered as the top product in an amount of 1,522 per hour and is then returned via line (17) into extraction system (12). In addition to benzene, 0.72 g per hour of water are obtained as the distillate from column (45). The sump product from column (45), which essentially consists of propionic acid, passes via line (46) into distillation column (47), which is operated in vacuo. Here, 261.5 g per hour of propionic acid are obtained as the top product and 260.1 per hour of this propionic acid are recycled via line (2) into reaction system (1), whilst the remaining amount of 1.4 g per hour is used, after adding appropriate amounts of fresh propionic acid, to prepare the stabiliser solution which passes into the process via (27). 2.53 g per hour of propylene glycol dipropionate are withdrawn from the sump of column (47) via (48) and passed, without further working up, to a suitable further use.

The yield of propylene oxide is 98.7% relative to the perpropionic acid fed into reaction system (31) and 94.75% relative to the hydrogen peroxide fed into the process at (1). The losses of propionic acid are 1.35% of the total amount fed into the process via (2) and (27), of 0.75% of this feed amount being contained in propylene glycol dipropionate. Losses of benzene are not detectable.

62.5 g per hour (= 44.81%) of the amount of propylene (145.5 g) fed per hour into reaction system (31) are recovered and recycled to the reaction stage (31); 54.84% are contained in the amount of propylene oxide obtained per hour. The amounts of propylene which are contained in the propylene glycol dipropionate are 0.56 g, which corresponds to a loss of 0.38%, relative to the amount of propylene fed in per hour via (32).

What is claimed is:

1. Process for the continuous production of propylene oxide from propylene and aqueous hydrogen peroxide which comprises:
    (a) contacting aqueous hydrogen peroxide with propionic acid for reaction of hydrogen peroxide and propionic acid to form perpropionic acid, in the presence of a water-soluble acid catalyst for the reaction, the amount of water, catalyst and hydrogen peroxide corresponding to an aqueous solution of catalyst and hydrogen peroxide containing 10 to 40% by weight of catalyst and 20 to 30% by weight of hydrogen peroxide, and the molar ratio of hydrogen peroxide to propionic acid being 3.5 to 5:1, at a temperature of 10 to 70° C.
    (b) extracting the resulting reaction mixture with benzene for formation of benzene phase rich in perpropionic acid, propionic acid, and containing hydrogen peroxide, and aqueous raffinate phase rich in hydrogen peroxide and catalyst,
    (c) treating at least part of the aqueous raffinate to remove water therefrom and form a concentrated solution of hydrogen peroxide and catalyst,
    (d) recycling said concentrated solution of hydrogen peroxide and catalyst to step (a),
    (e) extracting the benzene phase of step (b) with water for formation of a benzene phase containing perpropionic acid, propionic acid, water and a reduced amount of hydrogen peroxide, and an aqueous phase containing hydrogen peroxide.
    (f) subjecting the benzene phase produced in step (e) to azeotropic distillation to reduce the water content thereof to less than 0.5% by weight.
    (g) contacting the benzene phase of reduced water content of step (f) with propylene at a temperature of 40 to 100° C and a pressure of 2 to 30 bars for reaction of perpropionic acid of the benzene phase with propylene to form propylene oxide and a reaction mixture containing the propylene oxide, and other materials,
    (h) distilling the reaction mixture to distill overhead propylene, propylene oxide and benzene and removing bottoms comprising benzene and propionic acid;
    (i) subjecting the overhead from step (h) to a second distillation to distill off overhead propylene and recycling said propylene to step (g);
    (j) introducing the bottoms consisting essentially of propionic acid and benzene from the distillation of step (i) to a third distillation and distilling off overhead benzene and recycling said benzene to step (b).
    (k) removing bottoms from said third distillation consisting essentially of propionic acid and materials of higher boiling point than propionic acid and introducing said bottoms into a fourth distillation and distilling over propionic acid and recycling said propionic acid to step (a) and separating bottoms consisting essentially of the material of higher boiling point than propionic acid, and
    (l) recovering propylene oxide as a side cut from said second distillation.

2. Process of claim 1, wherein the watersoluble acid catalyst in step (a) is sulfuric acid.

3. Process of claim 2, wherein, in step (a), the amount of water, catalyst and hydrogen peroxide corresponds to an aqueous solution of catalyst and hydrogen peroxide of 23 to 28% by weight of catalyst and 22 to 28% by weight of hydrogen peroxide.

4. Process of claim 1, wherein, in step (a), the molar ratio of $H_2O_2$ : propionic acid is 3.7 to 4.5 : 1.

5. Process of claim 1, wherein, in step (a), the temperature is 20 to 60° C.

6. Process of claim 1, wherein, in step (a), the temperature is 30 to 40° C.

7. Process of claim 1, wherein, in step (b), the ratio of benzene to the reaction mixture is 0.3 to 4:1.

8. Process of claim 1, wherein, in step (b) the benzene used for the extraction contains less than 0.5% of propionic acid.

9. Process of claim 1, wherein, in step (b), the temperature is 10 to 70° C.

10. Process of claim 1, and dividing the aqueous raffinate of step (b) into two streams which are in a ratio of 2 to 5:1,
recycling the larger stream to step (a),
extracting the smaller stream with benzene using the inert solvent in a ratio of benzene to the smaller stream of 1 : 1 to 4 : 1, to produce an extract comprising the benzene and aqueous raffinate,
employing said extract as the benzene used in step (b), and
employing the aqueous raffinate from the extraction of said smaller stream as the aqueous raffinate treated in step (c).

11. Process of claim 10, wherein the extraction of step (b) is countercurrent and the extraction of the smaller stream is countercurrent.

12. Process of claim 1, wherein, in step (c), the aqueous raffinate distilled to remove water therefrom is distilled at 40 to 150 mm Hg and at a temperature of 60 to 85° C.

13. Process of claim 1, wherein, in step (c), the aqueous raffinate is distilled to remove therefrom water containing less than 0.1 percent by weight of hydrogen peroxide.

14. Process of claim 1, wherein 0.1 to 6% by weight of the aqueous raffinate of step (b) is withdrawn.

15. Process of claim 14, wherein the withdrawn aqueous raffinate contains hydrogen peroxide and sulfuric acid, and is regenerated for recovery of hydrogen peroxide and sulfuric acid.

16. Process of claim 15, wherein the hydrogen peroxide and sulfuric acid recovered in said regeneration is recycled for use in step (a).

17. Process of claim 1, wherein the benzene phase subjected to extraction in step (e) contains 7 to 15% by weight perpropionic acid.

18. Process of claim 1, wherein, in step (e), the amount of water used for extraction of the benzene phase is 0.5 to 3 percent by volume of the benzene phase subjected to the extraction.

19. Process of claim 1, wherein an aqueous phase is formed in the azeotropic distillation of (f), and the aqueous phase of step (f) is used in step (e) to provide water for the extraction of step (e).

20. Process of claim 1, wherein the aqueous phase containing hydrogen peroxide produced in step (e) is recycled to step (b).

21. Process of claim 1, wherein, in step (f), the temperature of the azeotropic distillation is 30 to 80° C, and the pressure is 100 to 400 mm Hg.

22. Process according to claim 1, wherein, in step (f), the water content of the benzene phase is reduced to less than 0.1% by weight.

23. Process of claim 1, wherein, in step (g), the molar proportion of propylene: perpropionic acid subjected to said contacting is 1.01 to 8:1.

24. Process of claim 1, wherein, in step (g), the temperature is 60 to 80° C.

25. Process of claim 1, wherein, in step (g), the molar proportion of propylene: perpropionic acid subjected to said contacting is 2 to 3:1.

26. Process of claim 1, wherein, in step (g), the contacting is performed in a reaction system which acts as a cascade of 10 to 30 ideally mixed kettles.

27. Process according to claim 26, wherein in step (g), the contacting is performed in said reaction system which acts as a cascade of 3 to 6 kettle reactors.

28. Process of claim 1, wherein in step (g), said contacting is performed at least partially in a tubular reactor.

29. Process of claim 1, wherein, in step (g), said contacting is partially carried out in a delay tube fitted with perforated baffle plates.

30. Process of claim 1, wherein, in step (a) hydrogen peroxide and propionic acid react to form said perpropionic acid and water, said water is removed in step (c), and make up hydrogen peroxide is included in said concentrated solution of hydrogen peroxide recycled to step (a) in step (d).

31. Process of claim 1, and dividing the aqueous raffinate of step (b) into two streams, recycling one of the streams to step (a), and employing the other of the streams as aqueous raffinate treated in step (c).

32. Process of claim 1, wherein:
in step (a), the water-soluble acid catalyst is sulfuric acid, the molar ratio of $H_2O_2$ : propionic acid is 3.7 to 4:5 : 1, the temperature is 20 to 60° C.
in step (b), the ratio of benzene to the reaction mixture is 0.3 to 4:1, the benzene used for the extraction contains less than 0.5 percent of propionic acid, the temperature is 10 to 70° C,
in step (c) the aqueous raffinate is distilled to remove water therefrom at 40 to 150 mm Hg and at a temperature of 60 to 85° C,
in step (e), the amount of water used for extraction of the benzene extract is 0.5 to 3 percent by volume of the benzene phase subjected to the extraction,
in step (f), the temperature of the azeotropic distillation is 30 to 80° C, and the pressure is 100 to 400 mm Hg, and the water content of the benzene phase is reduced to less than 0.1% by weight,
in step (g), the molar proportion of propylene: perpropionic acid subjected to said contacting is 1.01 to 8:1, and the temperature is 60 to 80° C.

* * * * *

UNITED STATES PATENT AND TRADEMARK OFFICE
CERTIFICATE OF CORRECTION

PATENT NO. : 4,137,242
DATED : January 30, 1979
INVENTOR(S) : Günter Prescher et al It is certified that error appears in the above-identified patent and that said Letters Patent are hereby corrected as shown below:

Column 4, line 62, "orthphosphate" should read -- orthophosphate --.
Column 8, line 40, "phosorus" should read -- phosphorus --.
Column 10, line 21, "of" should read -- or --.
Column 10, line 50, "in" should read -- In --.
Column 17, line 67, "a" should read -- and --.
Column 21, line 46, after "260.1" insert -- g --.

Signed and Sealed this

Twenty-fourth Day of July 1979

[SEAL]

Attest:

LUTRELLE F. PARKER
Attesting Officer    Acting Commissioner of Patents and Trademarks